(12) United States Patent
Perosi

(10) Patent No.: US 12,053,168 B2
(45) Date of Patent: Aug. 6, 2024

(54) MEDICAL DEVICE FOR CONCURRENT COLLECTION OF MULTIPLE TISSUE SAMPLES

(71) Applicant: Nicholas Perosi, Tinton Falls, NJ (US)

(72) Inventor: Nicholas Perosi, Tinton Falls, NJ (US)

(*) Notice: Subject to any disclaimer, the term of this patent is extended or adjusted under 35 U.S.C. 154(b) by 419 days.

(21) Appl. No.: 17/069,422

(22) Filed: Oct. 13, 2020

(65) Prior Publication Data

US 2022/0110614 A1   Apr. 14, 2022

(51) Int. Cl.
*A61B 10/02*   (2006.01)

(52) U.S. Cl.
CPC .. *A61B 10/0283* (2013.01); *A61B 2010/0225* (2013.01)

(58) Field of Classification Search
CPC .............. A61B 10/0283; A61B 2010/0225
See application file for complete search history.

(56) References Cited

U.S. PATENT DOCUMENTS

| 5,415,182 A * | 5/1995 | Chin ................... A61B 10/0275 |
| | | 600/564 |
| 6,146,594 A * | 11/2000 | De Graaff ............ B01L 3/0217 |
| | | 73/864.11 |
| 2010/0280408 A1* | 11/2010 | Rusnak .............. A61B 10/0266 |
| | | 600/567 |
| 2016/0000415 A1* | 1/2016 | Belsky ................... A61B 10/04 |
| | | 600/567 |
| 2018/0256138 A1* | 9/2018 | Araujo ............... A61B 10/0266 |
| 2019/0374247 A1* | 12/2019 | Paradis ............. A61M 25/0606 |

* cited by examiner

*Primary Examiner* — Rene T Towa
(74) *Attorney, Agent, or Firm* — Lowenstein Sandler LLP

(57) ABSTRACT

A medical device configured to enable concurrent collection of two tissue samples associated with an area of interest. The medical device can include a first needle hub having a fixed position and a second needle hub having an adjustable position. A position of the second needle hub can be adjusted using an adjustment mechanism of the medical device. The medical device can include an aspiration mechanism (e.g., a bulb) with tubing connecting the individual needles to create a suction mechanism to collect samples via aspiration.

16 Claims, 8 Drawing Sheets

MEDICAL DEVICE FOR CONCURRENT COLLECTION OF MULTIPLE TISSUE SAMPLES

TECHNICAL FIELD

Embodiments of the disclosure relate generally to diagnostic tissue biopsy, and more specifically, relate to a method and system of fine needle aspiration biopsy for concurrent collection of multiple tissue samples.

BACKGROUND

Traditional tissue biopsy remains one of the most definitive tests for diagnosis of cancer and other pathological diseases. Tissue biopsy requires a diagnostic tissue sample from a located lesion that is harvested, processed, and analyzed to determine the characteristics of the lesion. The development of non-invasive or minimally invasive assays has provided various options for diagnosing certain types of cancer and other diseases without the need for more invasive procedures.

Tissue samples from small organs or glands, such as lymph nodes or thyroid glands, are especially difficult to harvest due to their relatively small size, and proximity to significant solid organs and blood vessels. The considerable vascularization in many glands or organs increases bleeding risk when attempting to sample tissue with traditional open surgical biopsy. There are three different types of biopsy procedures to obtain sufficient tissue samples for pathologic characterization.

Open surgery is one type of procedure where an incision is made to expose the tissue from which a sample is required. Open surgery, however, is invasive and creates a considerable risk of infection, long recovery time, and high financial costs compared to less-invasive procedures. For those reasons, many practitioners tend to avoid open surgery biopsies.

A second type of procedure is a core needle biopsy (CNB) which requires removal of a relatively large piece of tissue from the area of interest. Typically under ultrasound or computed tomography (CT) guidance and local anesthesia, a semi-automated device with a spring-loaded mechanism dispenses a needle to obtain a core sample. The cored sample is large enough that it requires further processing, including slicing of the sample to analyze under a microscope. The CNB approach is typically employed when a large sample is needed, however failure to obtain an adequate sample may require multiple attempts. This procedure is less invasive than open surgery, but has been associated with higher risk of bleeding, swelling, or bruising than other approaches, such as fine needle aspiration.

Similar to CNB, fine needle aspiration (FNA) removes smaller samples of tissue using a needle under ultrasound or CT guidance without the need for open surgery. The samples are smaller than CNB and do not require further processing before microscopic analysis. During an FNA procedure, a patient may or may not be given a local anesthetic. A needle, typically 20-30 gauge, is inserted hypodermically and positioned into the targeted tissue where it may penetrate fat and muscular tissue depending on the location. Tissue sample is then drawn into the needle via aspiration or by capillary action. Aspiration occurs by using a suction mechanism to draw cellular material into the needle. Capillary action occurs by moving the needle back and forth to draw tissue samples into the needle. The needle is then withdrawn from the patient and the tissue collected is placed on a slide for pathological analysis.

The FNA process is typically repeated multiple times to obtain a sufficient number of samples for testing purposes (e.g., about four slides with tissue samples). Commonly the aspirations are performed consecutively and handed to the pathology team for analysis. Disadvantageously, the need to perform multiple iterations of the aspiration steps increases the risk to the patient and discomfort associated with the sample collection process.

BRIEF DESCRIPTION OF THE DRAWINGS

The included drawings are for illustrative purposes and serve to provide examples of possible structures and operations for the disclosed inventive systems, apparatus, methods, and computer-readable storage media. These drawings in no way limit any changes in form and detail that may be made by one skilled in the art without departing from the spirit and scope of the disclosed implementations.

DETAILED DESCRIPTION

Figure 1:
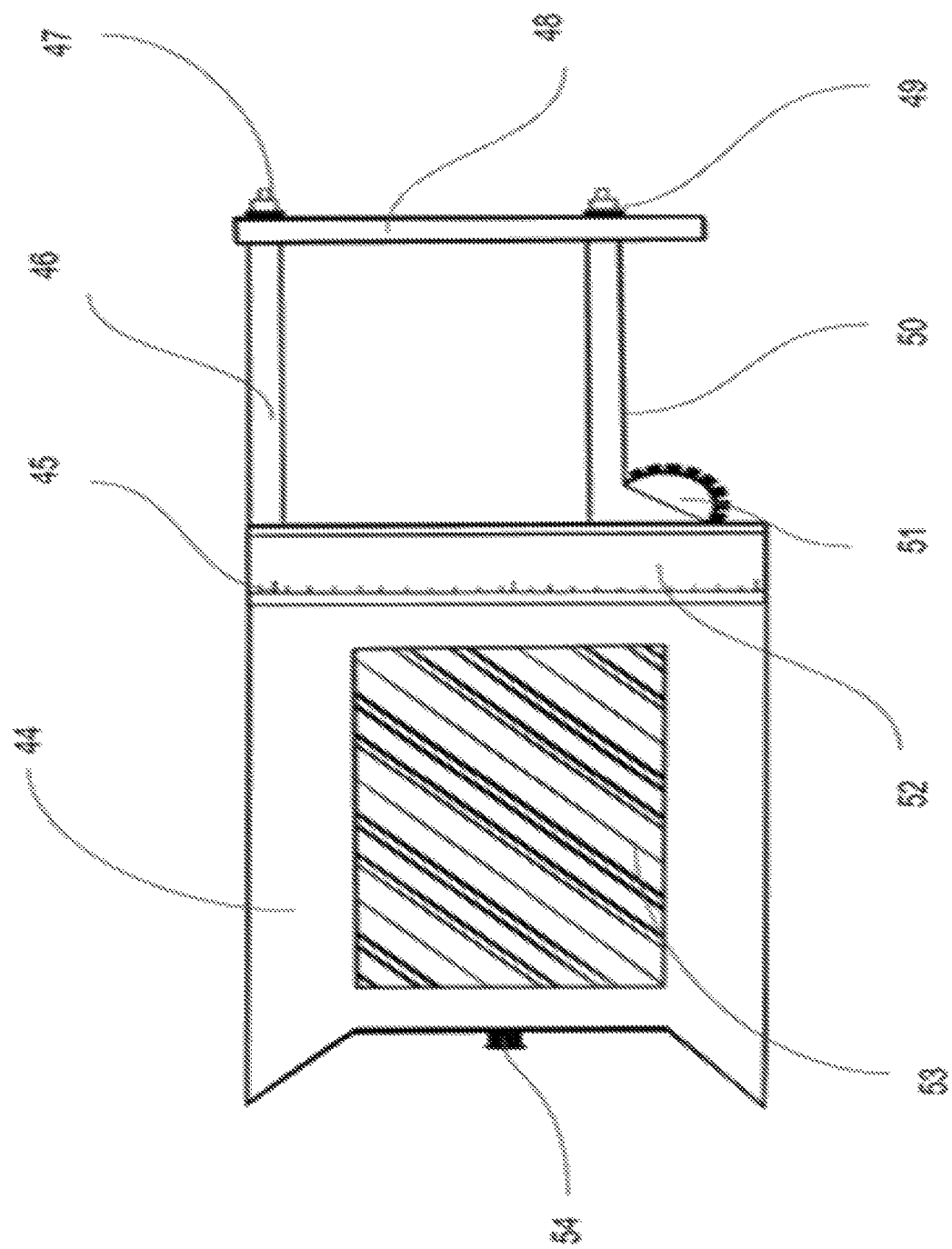
FIG. 1 shows an example device to enable concurrent collection of multiple tissue samples, in accordance with one or more implementations.

The present disclosure relates to a medical device to enable simultaneous tissue sampling of multiple different portions of an area of interest (e.g., two different portions of a lesion) for use in a thorough pathological analysis. The medical device is configured to include multiple needle portions using a lock mechanism. In an embodiment, the medical device includes a first needle and a second needle using a lock mechanism such as a luer lock mechanism. In an embodiment, the medical device includes a handle portion configured to be held by an end user (e.g., a medical professional). According to embodiments of the present disclosure, the medical device is adapted to secure multiple standard gauge needles for collection of a tissue sample of a subject (e.g., a patient). In an embodiment, the medical device includes multiple needle hubs secured within a support bracket to secure their position within the device. In an embodiment, the needle hubs are an integrated structural component of the medical device (e.g., do not need to be added by a separate attachment).

In an embodiment, the medical device includes a first needle hub maintained or positioned at a constant position (herein a "first needle" or "needle #1"). In an embodiment, the medical device includes a second needle hub (herein a "second needle" or "needle #2") that is positioned a distance (e.g., 5 mm) away from the first needle hub. In an embodiment, the distance between the first needle and the second needle can be measured from the respective needle tips. In an embodiment, the second needle hub has an adjustable position to enable a range of positions and distances from the first needle. For example, the first needle hub (and corresponding first needle when attached) are at a set position. The second needle hub (and corresponding second needle when attached) can be adjustably positioned relative to the first needle hub within a distance range (e.g., a minimum distance to a maximum distance relative to the first needle hub). For example, the second needle hub can be adjustably positioned at a distance of approximately 5 mm from the first needle hub to a distance of approximately 20 mm from the first needle hub.

In an embodiment, the minimum distance and the maximum distance can be any suitable values. For example, the medical device can be configured to enable multiple different maximum distances, such as 20 mm to 100 mm. In an embodiment, positioning of the second needle can be adjusted in set increments (e.g., 1 mm increments between the minimum distance and the maximum distance). In an embodiment, the position of the second needle can be adjusted continuously (e.g., without set increments) from the minimum distance to the maximum distance. In an embodiment, the distance between the first needle and the second needle can be measured and identified by a user with a standard measuring ruler (metric) built into the handle of the medical device. In an embodiment, the positon of the second needle can be adjusted using any suitable adjustment mechanism, such as, for example, a rolling wheel mechanism.

According to embodiments, the medical device includes a suction mechanism extending from the multiple needle hubs (e.g., the first needle hub and the second needle hub) into the handle to allow for aspiration action to be executed by a user. In an embodiment, the suction mechanism is built into the handle as a bulb or other similar structure (e.g., a cavity configured to which the end user can squeeze to aspirate tissue samples once the needles are in place. In an embodiment, an end user can execute a capillary action (as opposed to aspiration) by foregoing the use of the bulb structure and instead moving the medical device back and forth to obtain sufficient tissue samples.

In an embodiment, the medical device includes an air valve located at an end portion (e.g., butt cap) of the handle. In operation, turning the air valve allows air to flow back into the bulb structure. In an embodiment, the tissue samples within the multiple needles can be retrieved by applying a force to the bulb (e.g., squeezing the bulb) and placing tissue samples onto glass slides. Advantageously, the multiple tissue samples are collected simultaneously. In this regard, when two locations within the target area (e.g., a lesion) are biopsied at the same time, patient discomfort and procedure time are decreased, while the sample size is multiplied. In addition, the medical device allows for safer passage of needles between the individuals conducting the biopsy and receiving the samples for analysis.

Furthermore, the medical device improves FNA tissue biopsy procedures by providing for the insertion of multiple needles simultaneously, thereby decreasing procedure time, decreasing pain from procedure, decreasing risk of infection, and improving sampling of lesions for pathological analysis. The concurrent sampling is advantageous because it requires prepping the patient once, a single insertion action, and a single removal of the needles, thereby decreasing the risk of infection with consecutive needles passing through and less overall damage to the surrounding tissues. By simultaneously deploying multiple needles to gather sample tissues, the tissue collection procedure is more time efficient.

According to embodiments, the medical device can utilizes standard hypodermic needles for fine needle aspiration or capillary action. By using standard needle designs, the medical device of the present disclosure is able to accommodate for any standard needle gauges that are readily available or use with the medical device.

In an embodiment, using an ultrasound guided technique, one can measure the size of the target area (e.g., a size of a lesion) and adjust the second needle to a desired position. Advantageously, the concurrent sampling technique enabled by the medical device of the present disclosure collects different tissue samples (via each of the respective needles) of different areas of the lesion to provide better diagnostic tissue samples for pathology analysis. In this regard, according to another advantage, the two needles of the medical device collect samples that are different from one another. In an embodiment, the end user can move the medical device back and forth per their normal aspiration protocol to collect tissue samples using capillary action.

According to an embodiment, the medical device includes multiple needles (e.g., a first needle and a second needle) that are attachable to integrated hubs extending from a main body of the medical device, without the use of an additional external adapter hubs. The use of the integrated hubs provides for a safer protocol for the end user as it minimizes the risk of needles unintentionally hurting someone. In addition, the medical device have integrated needle hubs reduces the risk of damaging the needles. Furthermore, passage of the collected tissue samples to a next phase of the analysis (e.g., a pathology team) can be executed in a safer manner by minimizing the quantity of needles being passed from person to person. For example, in an embodiment, in use, the medical device can be fabricated such that the medical device is disposed of into an appropriate container (e.g., a sharps container) after tissue collection and retrieval is complete.

In an embodiment, the medical device includes a built-in suction mechanism for the collection of samples using aspiration, similar to a suction action associated with the operation of a syringe. This mechanism is built into the handle so that the suction effect can be done with the same hand that the device is being held in. This allows the user to continue holding the ultrasound scanner with one hand and simultaneously create a suction effect with the other hand holding the device. In an embodiment, the handle portion of the medical device encases a squeezable bulb portion that is located centrally and easily accessible to the end user. In an embodiment, the medical device includes a tubing portion (e.g., plastic tubing) extending from each of the multiple needle hubs into the cavity of the bulb.

During operation of the medical device, an end user can squeeze the bulb portion to draw tissue samples into the needles through aspiration. Once tissue collection is complete, the medical device including the collected samples can be provided to a subsequent stage of the process (e.g., a pathology team for retrieval of the samples from within the needles). As noted above, a portion of the handle contains an air valve that enables air to flow back into the bulb. In an embodiment, a user (e.g., a pathologist) can press the bulb to release the tissue samples from the needles onto one or more slides for further analysis.

In an embodiment, the air valve can include a lock mechanism (e.g., a luer lock mechanism). In this embodiment, the lock mechanism can be used for attachment of a syringe onto the air valve for additional suction capabilities. According to embodiments, aspiration of tissue samples can proceed through a standard fine needle aspiration protocol.

FIG. 1 illustrates an aspects and elements of a medical device according to embodiments of the present application. As shown in FIG. 1, the medical device includes a first needle hub 47 (also referred to as a "first needle engagement portion") and a second needle hub 49 (also referred to as a "second needle engagement portion"). In an embodiment, the needle hubs 47, 49 are portions of the medical device that provide for engagement or attachment of one or more needles (not shown in FIG. 1). In an embodiment, the needle hubs 47, 49 can be supported by a bracket 48. In an embodiment, the bracket 48 includes a track or channel within which the second needle hub 49 can traverse in response to an adjustment of the position of the second needle hub 49.

In an embodiment, the first needle hub 47 is configured in a fixed position. In an embodiment, a position of the second needle hub 49 is adjustable using a position adjustment mechanism, such as, for example, a rolling or adjustment wheel 51. In an embodiment, the medical device can include markings or indicators (e.g., metric marks) 52 to indicate a position of the second needle hub 49. In an embodiment, the indicators 52 can represent a distance between the first needle hub 47 and the second needle hub 49. In an embodiment, the bracket 48 can include a channel that enables the second needle hub 48 to traverse in response to adjustment of the position of the second needle hub 48. In an embodiment, the medical device includes a scaffold portion 52 along which the adjustable second needle hub 48 can traverse.

Figure 4:
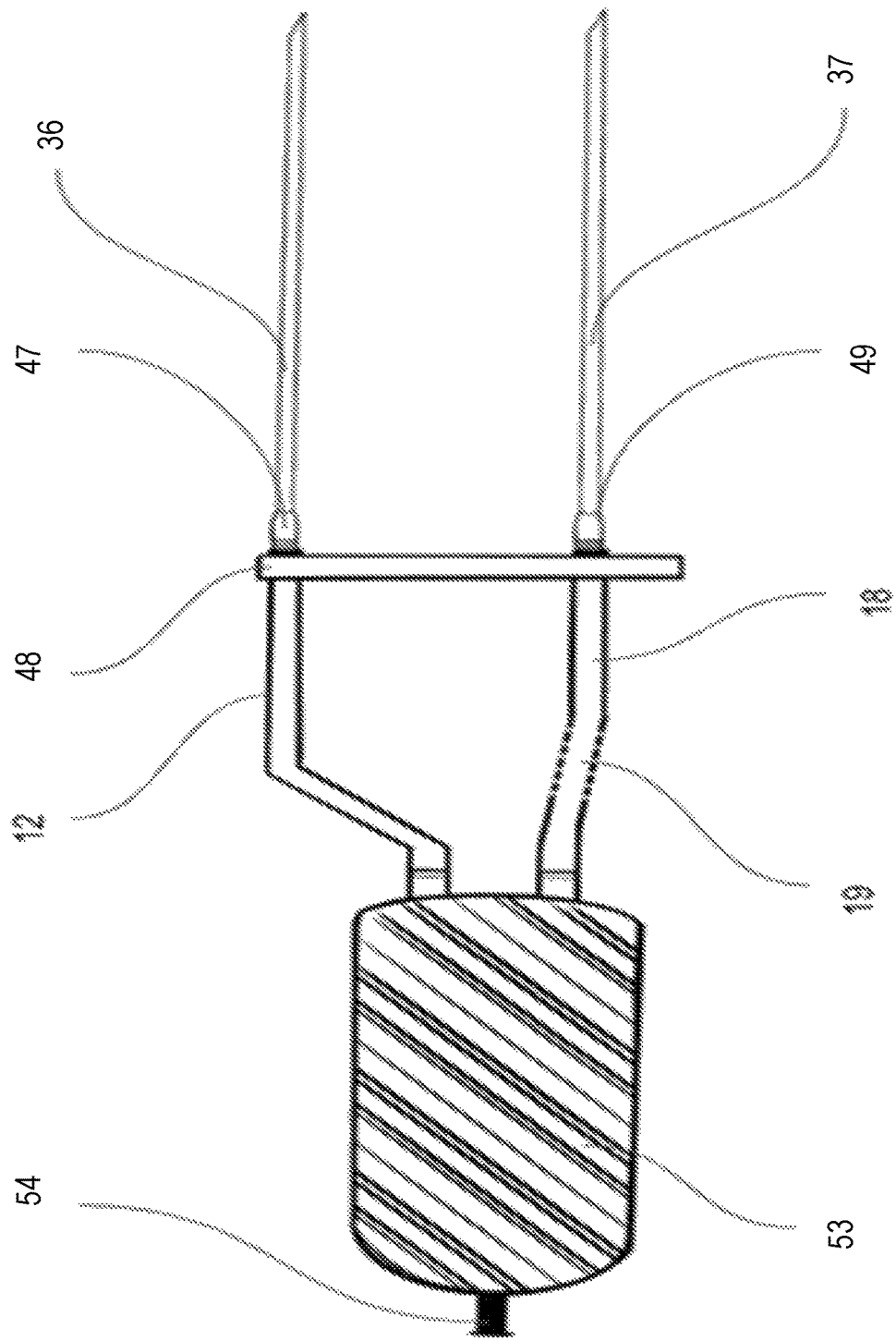
FIG. 4 illustrates an example device to execute an aspiration operation using a tubing structure extending from a bulb element to multiple needle hub structures, in accordance with one or more implementations.

In an embodiment, the medical device includes a bulb 53 (also referred to as an "aspiration structure") or other cavity configured to enable interaction (e.g., a squeezing action) by a user. The bulb 53 is operatively coupled to the first needle hub 47 and the second needle hub 49 (as illustrated in FIG. 4) to enable aspiration of a target area and the collection of a set of tissue samples in the bulb 53 (e.g., a first portion collected via a first needle attached at the first needle hub 47 and a second portion collected via a second needle attached at the second needle hub 49). In an embodiment, the bulb 53 may include a multi-function grip surface to enable a user to interact with the bulb 53 for the collection of the set of tissue samples.

In an embodiment, the medical device of FIG. 1 includes a handle having an adjustable proximal end 44 for use by an operator/use of the medical device. In embodiment, the medical device includes a non-adjustable (e.g., fixed) portion 46 extending between the handle 44 and the first needle hub 47. In an embodiment, the medical device includes an adjustable portion 50 extending between the handle and the second needle hub 47. In an embodiment, the medical device includes a knob 54 or other suitable structure and mechanism to allow the bulb 53 to refill with air in response to an operation action (e.g., when the knob 54 is turned). For example, an operator can turn the knob 54 to enable air to flow back into the bulb 53 when retrieving the collected set of samples.

Figure 2:
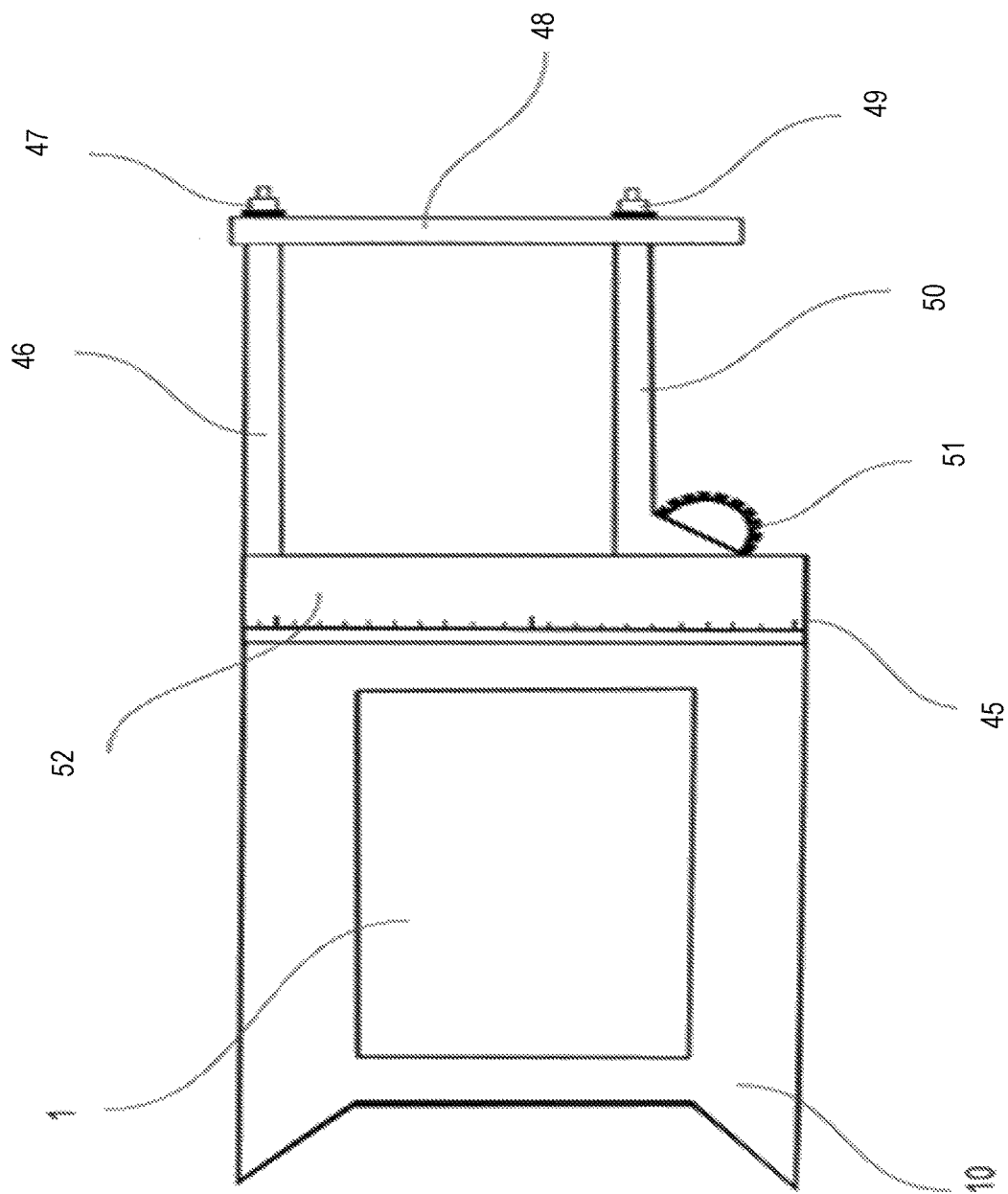
FIG. 2 shows an example perspective of a device to enable concurrent collection of multiple tissue samples, in accordance with one or more implementations.

FIG. 2 illustrates an example medical device in accordance with embodiments of the present disclosure. The example medical device is shown in FIG. 2 in a view without the aspiration mechanism. In an embodiment, the medical device includes a portion 1 configured to include the aspiration mechanism and enable an end user to hold onto a frame 10 of the medical device. In an embodiment, the medical device shown in FIG. 2 enables the execution of capillary action in an instance where a user elects to forego the aspiration functionality of the aspiration mechanism (e.g., the bulb 53 of FIG. 1).

Figure 3:
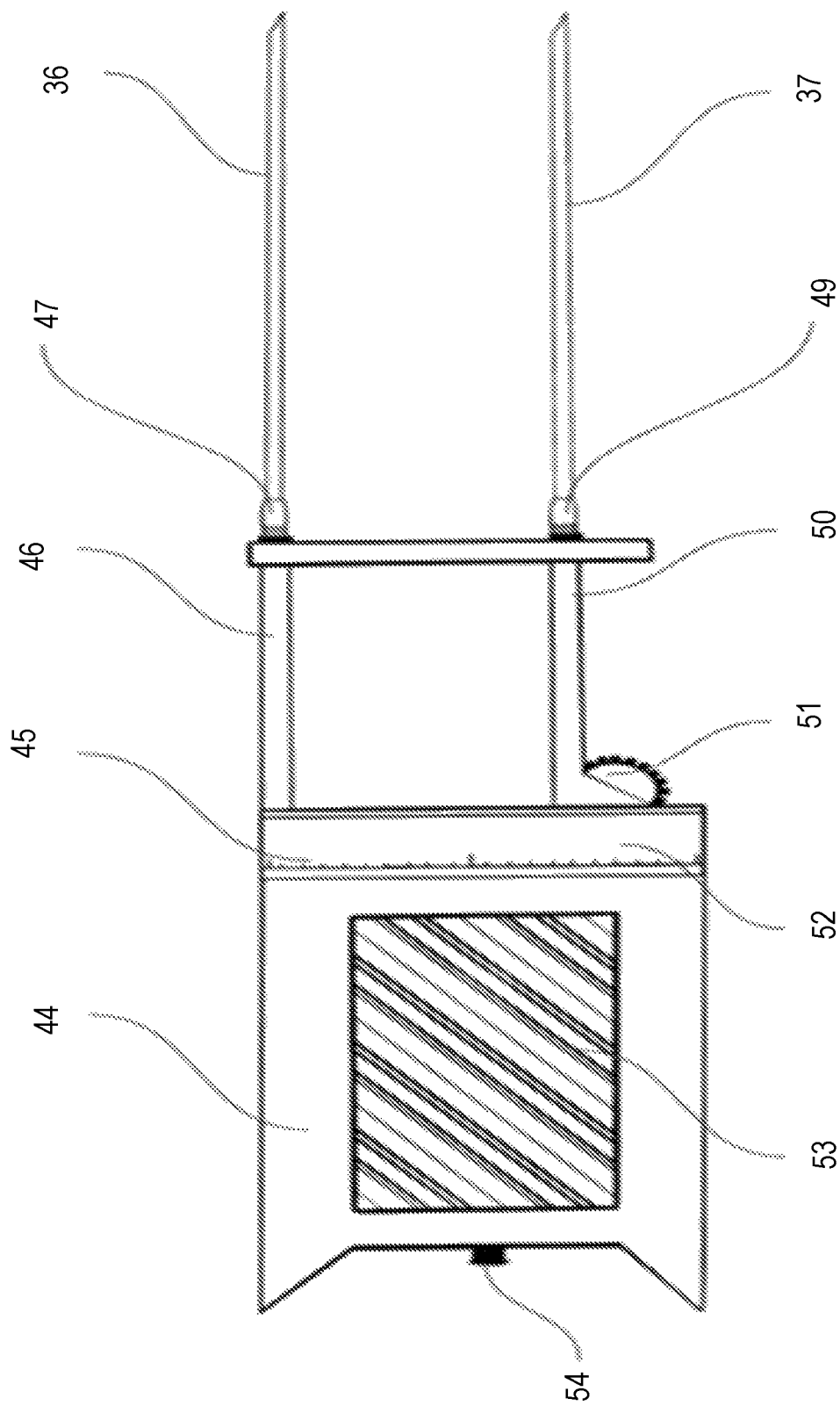
FIG. 3 shows an example device including a needle portion attached using a lock mechanism, in accordance with one or more implementations.

FIG. 3 illustrates an example medical device including a first needle 36 attached o coupled to the first needle hub 47 and a second needle 37 attached or coupled to the second needle hub 49, in accordance with embodiments of the present disclosure. In an embodiment, the first needle 36 and the second needle 37 (e.g., hypodermic needles) can be locked into attachment by the respective hubs 47, 49. In an embodiment, the first needle hub 47 and the second needle hub 49 can be locking mechanisms, such as luer lock mechanisms.

FIG. 4 illustrates portions of an example medical device including an underlying aspiration mechanism 53 operatively coupled to multiple needle hubs 47, 49, according to embodiments of the present disclosure. As shown, a first needle 36 is attached or connected to the first needle hub 47. The first needle hub 47 is connected to the aspiration mechanism (e.g., a bulb) 53 by a first tube portion or channel 12 extending there between. The second needle hub 49 is connected to the aspiration mechanism 53 by a second tube portion or channel 18.

In an embodiment, the tube portions 12, 18 extend from the needle hubs 47, 49 to allow for the passage of air to enable aspiration action for the collection and deposition of tissue samples. In an embodiment, the tube portions 12, 18 can be composed of any suitable material, including but not limited to plastic. In an embodiment, the second tube portion 18 can have a greater length than the first tube portion 12, as denoted in FIG. 4 by the dashed-line portion 19. In an embodiment, the different in the tube portion provides sufficient slack for movement along the medical device.

Figure 5:
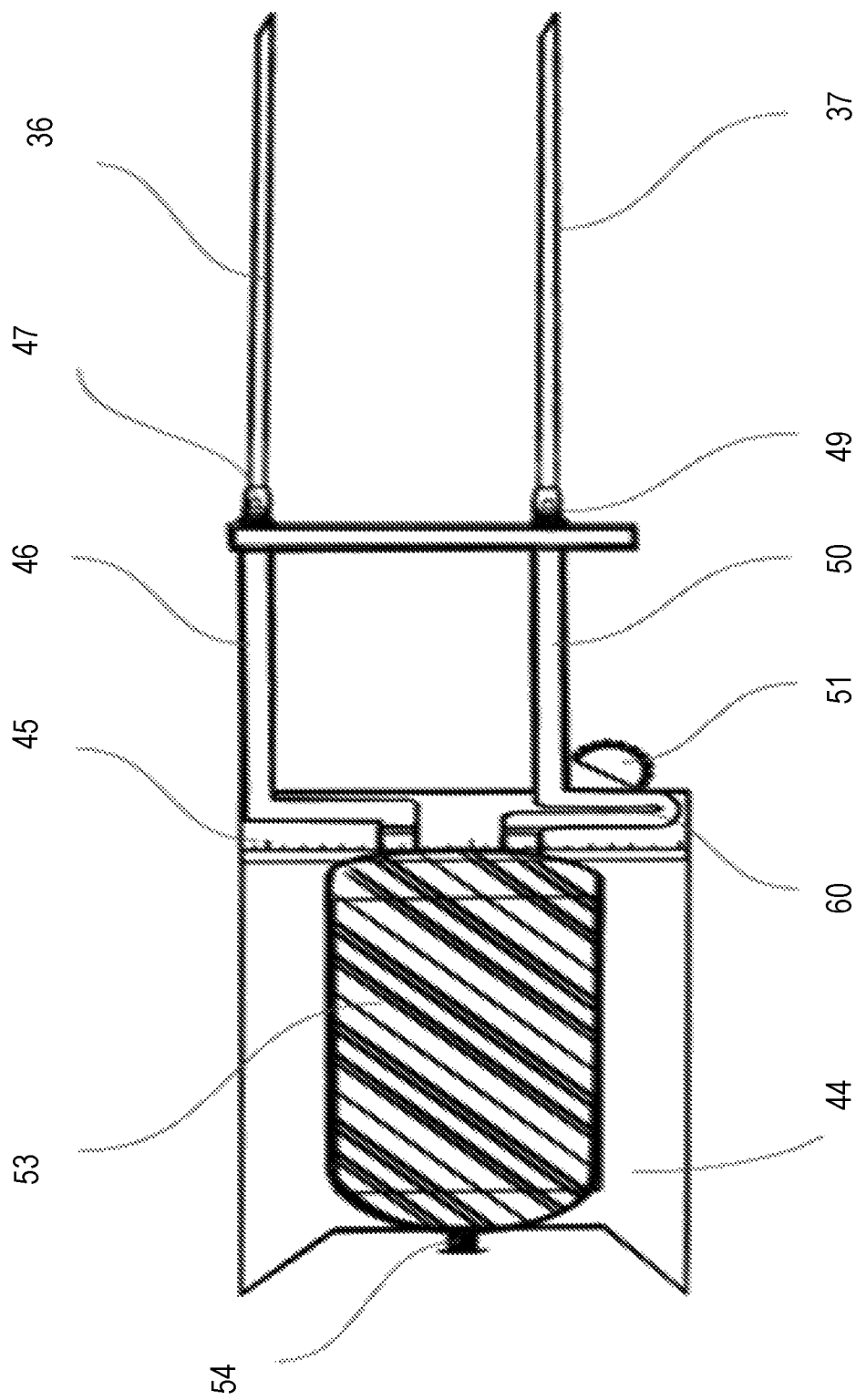
FIG. 5 illustrates an example device including an embedded aspiration system, in accordance with one or more implementations.
Figure 8:
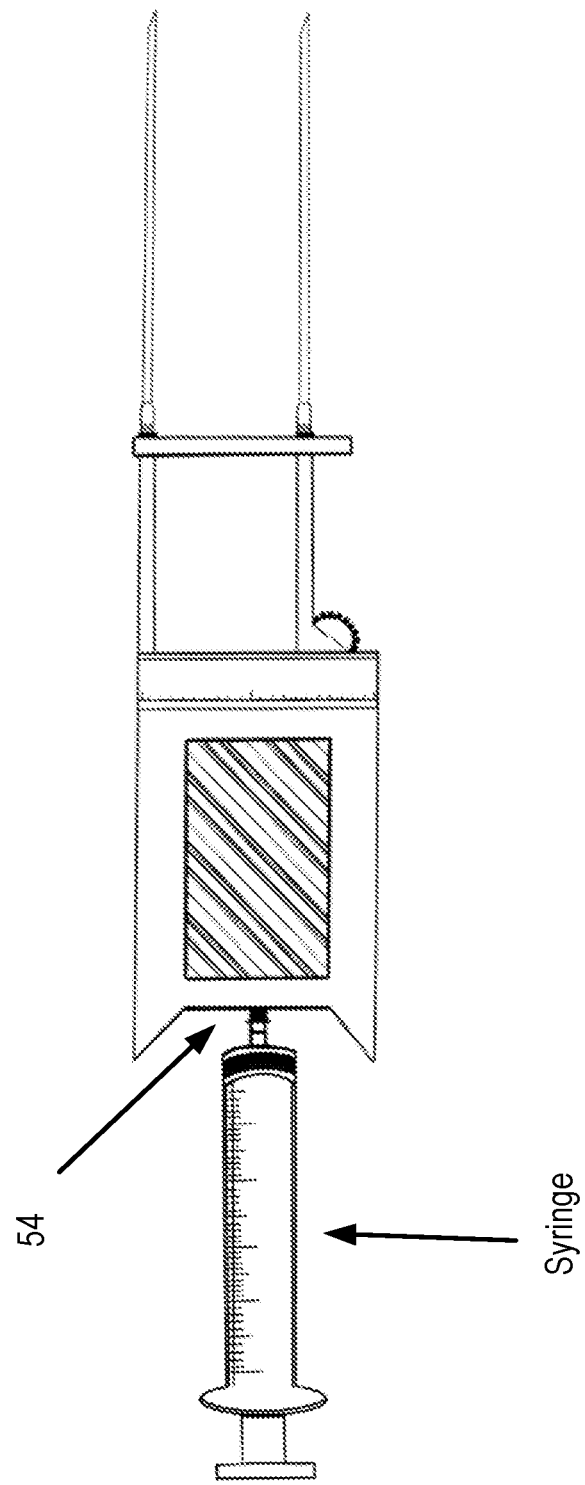
FIG. 8 is an example device including an air valve configured to engage with a syringe, in accordance with one or more implementations.

FIG. 5 illustrates a view of a medical device according to embodiments wherein an aspiration mechanism is embedded or integrated within a housing or exterior portion of the medical device. In an embodiment a user can hold a handle portion 44 of the medical device. Two needles 36, 37 (e.g., hypodermic needles) can be attached to the medical device at the respective needle hubs 47, 49. In an embodiment, the aspiration system 53 of the medical device can include a tubing portion 46, 50 extending between the needle hubs 47, 49 and the aspiration structure (e.g., bulb). In operation, squeezing the bulb 53 draws tissue up into the respective needles 36, 37 by aspiration. Air can be brought back into the bulb 53 by twisting the air valve 54 to enable the deposition of the collected samples from the needles (e.g., onto a slide) by squeezing the bulb 53. In an embodiment, as shown in FIG. 8, in accordance with fine needle aspiration protocol, a syringe can be attached to the air valve 54 through a locking mechanism (e.g., a luer lock mechanism). In an embodiment, as shown in FIG. 8, the syringe can be attached to the air valve 54 and act as a secondary support system to increase suction while aspirating or increase force to expel the tissue sample. In an embodiment the air valve 54 is configured to receive and engage with the syringe to enable the operation of the syringe to increase the suction during aspiration.

In an embodiment, the position of needle hub 49 (e.g., the second needle hub) can be adjusted using an actuation mechanism 51 (e.g., a rolling wheel) and set to a desired position using the indicators 22 (e.g., metric marks). In an embodiment, although a rolling wheel is shown as an exemplary actuation mechanism 51, it is noted that any suitable mechanism can be employed (e.g., a lever, a motorized component, a computer-operated actuator, etc.) In an embodiment, additional slack 60 can be provided in the second tubing portion 50 (as compared to the first tubing portion 46) to accommodate movement and positioning of the second needle hub 49.

Figure 6:
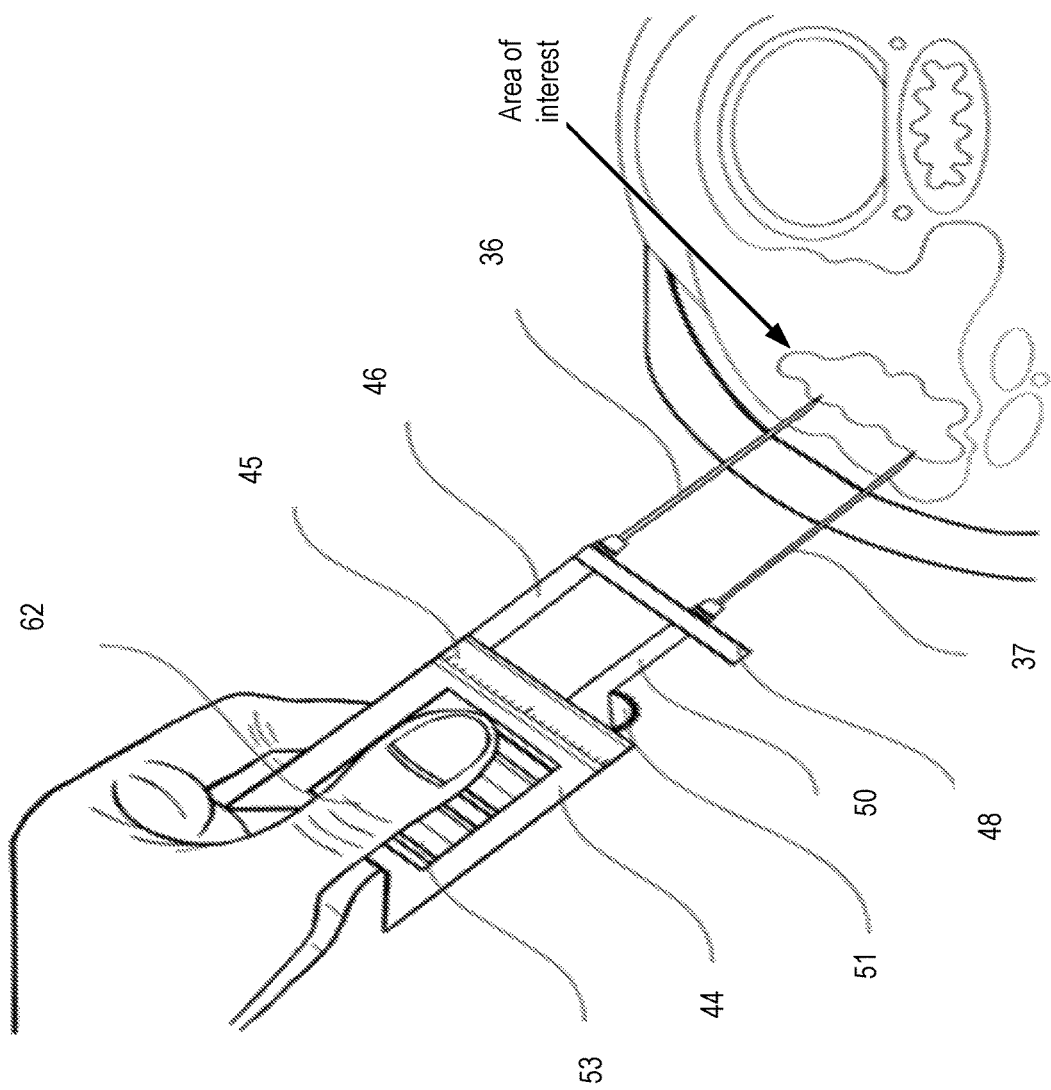
FIG. 6 illustrates an example device configured to collect multiple different samples from within a same subcutaneous lesion, in accordance with one or more implementations.

FIG. 6 illustrates a transverse view of an example medical device configured to collect a set of samples including multiple different samples from within a same subcutaneous target area (e.g., a lesion in a thyroid of a patient). FIG. 6 illustrates the medical device having a first needle 36 and a second needle 37 attached to respective needle hubs, with the 58, 59, with the second needle 37 adjusted to a desired position using the rolling wheel 61 and measured using the metric marks 45. The needles 36, 37 are supported by a bracket 48 to secure their position and inhibit extraneous movement. In an embodiment, the user can hold onto the handheld portion 44 of the medical device and move the medical device in and out to draw tissue up by capillary action. In an embodiment, the end user can squeeze or otherwise apply a force (e.g., using a thumb 62) to the bulb 64 to draw tissue up by aspiration, as described in detail above.

Figure 7:
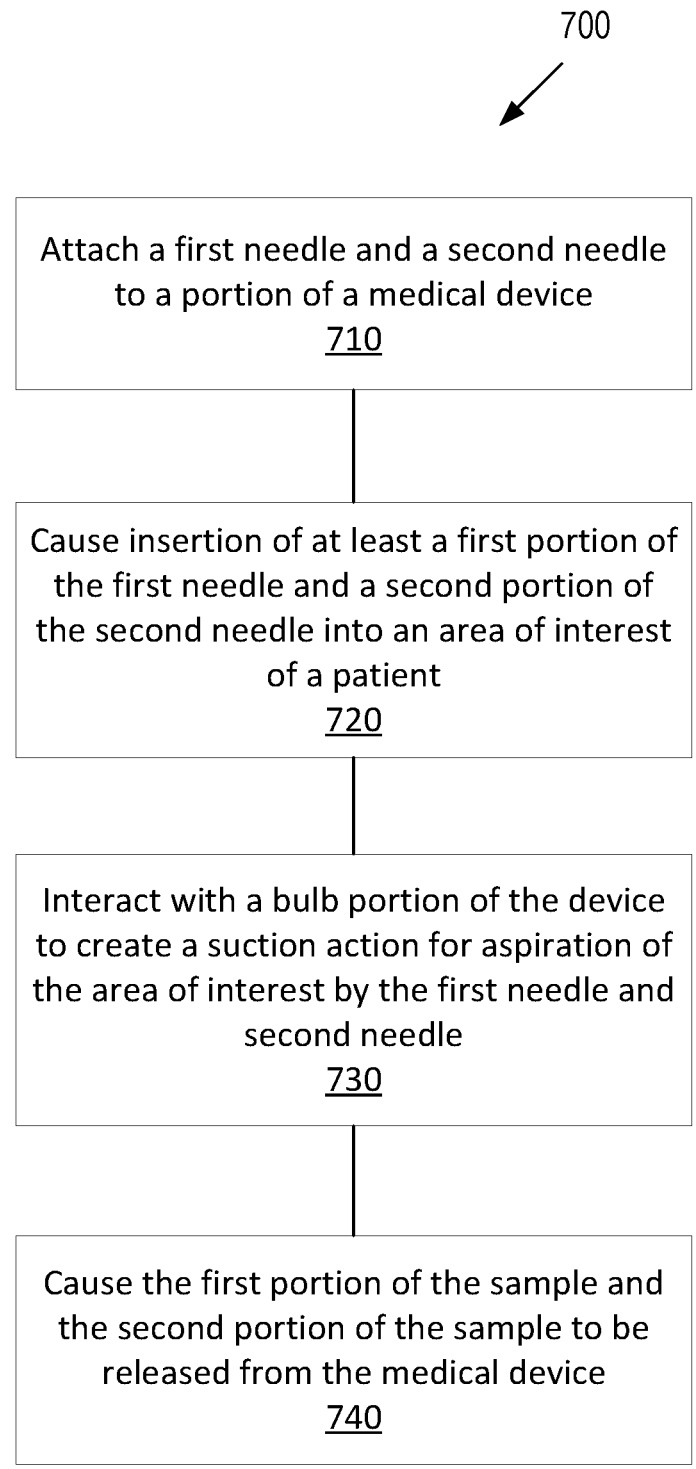
FIG. 7 is an example method of operation of a device to collect multiple tissue samples associated with an area of interest, in accordance with one or more implementations.

FIG. 7 illustrates an example method 700 of operation of a medical device in accordance with embodiments of the present application. In an embodiment, the method can be performed by a user of the medical device in connection with a procedure relating to a patient. In an embodiment, the procedure can include the collection of a set of tissue samples associated with an area of interest using multiple needles attached to respective needle hubs of a medical device according to embodiments of the present application.

In operation 710, a first needle and a second needle are attached to a portion of a medical device. In an embodiment, the first needle is locked into the medical device using a first needle hub. The first needle hub provides a port or engagement point for the first needle and includes a first locking mechanism (e.g., a luer locking mechanism) to lock or secure the first needle to or within the medical device. In an embodiment, the second needle is attached to the medical device via the second needle hub. The second needle hub provides a port or engagement point for the second needle and includes a second locking mechanism to secure the second needle to or within the medical device.

In an embodiment, a position of the second needle can be adjusted and set. In an embodiment, the position of the second needle hub is adjustable and can be moved relative to the fixed position of the first needle hub. In an embodiment, the second needle hub (and second needle) can be moved in preset increments (e.g., 1 mm increments) or in an analog manner.

In operation 720, insertion into an area of interest of a patient of at least a portion of the first needle and the second needle is caused. In an embodiment, the portions of the first and the second needle (e.g., end or tip portions) are advanced to a surface of the skin and caused to penetrate the area of interest. In an embodiment, the first and second needles are advanced into the area of interest by an operator moving the medical device through a corresponding action.

In operation 730, a suction action is caused for aspiration of the area of interest by the first needle and the second needle. In an embodiment, the suction action is caused by an interaction by a user with a bulb portion of the medical device. In an embodiment, the operator can squeeze or otherwise apply a force to the bulb to create the suction action via the tube portions operatively coupled first needle and second needle. In an embodiment, the suction action enables the aspiration of the area of interest by the first needle and the second needle.

In operation 740, release of the first portion of the sample and the second portion of the sample from the medical device is caused. In an embodiment, to release the sample portions, an operator can turn a knob (e.g., knob 54 of FIGS. 1, 3, 4, and 5) to open an air valve to allow air to fill in a bulb. In an embodiment, the air valve can be closed and a force can be applied to the bulb to enable the air in the bulb to traverse the channels to the needle hubs to expel the samples from the needles. In an embodiment, if the sample portions are thick or viscous, the needles can be removed to assist in the removal of the samples from the medical device.

What is claimed is:

1. A device comprising:
   a first needle engagement portion to secure a first needle comprising a first tip portion;
   a second needle engagement portion to secure a second needle comprising a second tip portion;
   an adjustment component coupled to the second needle engagement portion, wherein the adjustment component causes a sliding lateral adjustment of a position of the second tip portion of the second needle to set a selected lateral spacing between the first tip portion of the first needle and the second tip portion of the second needle, wherein the first tip portion remains in a fixed position during the sliding lateral adjustment of the position of the second tip portion of the second needle; and
   a handle portion comprising an aspiration structure, the aspiration structure comprising a cavity coupled to:
   the first needle engagement portion by a first tube portion; and
   the second needle engagement portion by a second tube portion;
   wherein actuation of the aspiration structure aspirates an area of interest using the first needle and the second needle to collect a set of tissue samples at the selected lateral spacing.

2. The device of claim 1, wherein the adjustment component causes movement of the second needle engagement portion from a first position to a second position.

3. The device of claim 1, wherein the position of the second needle engagement portion is adjustable relative to the fixed position of the first needle engagement portion.

4. The device of claim 1, further comprising a bracket coupled to the first needle engagement portion and the second needle engagement portion.

5. The device of claim 4, wherein the bracket comprising a channel in which the second needle engagement portion traverses in response to an adjustment of a position of the second needle engagement portion.

6. The device of claim 1, wherein the set of samples comprises a first sample associated with the first needle and a second sample associated with the second needle.

7. The device of claim 1, further comprising one or more indicators associated with a position of the second needle engagement portion relative to the first needle engagement portion.

8. The device of claim 1, further comprising:
   a first tube portion extending from the aspiration structure to the first needle engagement portion; and
   a second tube portion extending from the aspiration structure to the second needle engagement portion.

9. The device of claim 8, wherein a first length of the first tube portion is less than a second length of the second tube portion.

10. A medical device comprising:
   a first portion configured to engage a first needle;
   a second portion configured to engage a second needle;
   an adjustment component coupled to the second portion, wherein the adjustment component causes a sliding lateral adjustment of a position of the second needle to set a selected lateral spacing between the first needle and the second needle, wherein the first needle remains in a fixed position during the sliding lateral adjustment of the position of the second needle; and
   an aspiration structure coupled to:
      the first portion via a first connector; and
      the second portion via a second connector;
      wherein actuation of the aspiration structure aspirates an area of interest using the first needle and the second needle to collect a set of tissue samples at the selected lateral spacing.

11. The medical device of claim 10, wherein the first connector comprises a first tube and the second connector comprises a second tube.

12. The medical device of claim 10, wherein interaction with the aspiration structure causes a capillary action to collect a first tissue sample of the set of tissue samples via the first needle and a second tissue sample of the set of tissue samples via the second needle.

13. The medical device of claim 12, wherein the first tissue sample is drawn into the first needle and the second tissue sample is drawn into the second needle.

14. The medical device of claim 10, further comprising a bracket coupled to the first portion and the second portion, wherein the bracket comprising a channel in which the second needle traverses.

15. The medical device of claim 10, wherein the first needle is removable from the first portion and the second needle is removable from the second portion.

16. The medical device of claim 10, wherein the first portion comprises a first luer locking mechanism and the second portion comprises a second luer locking mechanism.

* * * * *